United States Patent [19]

Sakasai et al.

[11] Patent Number: 4,990,536

[45] Date of Patent: Feb. 5, 1991

[54] IMMUNOPOTENTIATOR AND SPERGUALIN-RELATED COMPOUND THEREFOR

[75] Inventors: Takeji Sakasai, Urawa; Tsugio Tomiyoshi, Tokyo; Keiko Watanabe, Kawaguchi; Kyuichi Nemoto, Tokyo; Tetushi Saino, Yono; Yoshihisa Umeda, Otsu, all of Japan

[73] Assignees: Nippon Kayaku Kabushiki Kaisha, Tokyo; Takara Shuzo Co., Ltd., Kyoto, both of Japan

[21] Appl. No.: 494,613

[22] Filed: Mar. 16, 1990

[30] Foreign Application Priority Data

Apr. 3, 1989 [JP] Japan .................................. 1-81633

[51] Int. Cl.$^5$ .......................................... A61K 31/195
[52] U.S. Cl. .................... 514/563; 564/157; 564/159; 514/620; 514/626; 562/439
[58] Field of Search .................. 514/563, 620, 626; 564/157, 159; 562/439

[56] References Cited

U.S. PATENT DOCUMENTS

| | | | |
|---|---|---|---|
| 4,416,899 | 11/1983 | Umezawa et al. | 564/159 |
| 4,430,346 | 2/1984 | Umezawa et al. | 564/159 |
| 4,518,532 | 5/1985 | Umezawa et al. | 564/159 |
| 4,525,299 | 6/1985 | Umezawa et al. | 564/159 |
| 4,556,735 | 12/1985 | Umezawa et al. | 564/157 |
| 4,851,446 | 7/1989 | Umlzawa et al. | 514/627 |

OTHER PUBLICATIONS

The Journal of Antibiotics, vol. XL, No. 9 (1987), pp. 1303-1315.

*Primary Examiner*—James H. Reamer
*Attorney, Agent, or Firm*—Henry C. Nields

[57] ABSTRACT

The present invention provides a use for the preparation of an immunopotentiator of a spergualin-related compound represented by the following general formula [I] or a pharmacologically acceptable salt thereof:

[I]

$H_2N-C-NH-X-(CH_2)_3-CO-NH-CH-CO-NH-R$
　　　$\|$　　　　　　　　　　　　　　　　$|$
　　　$HN$　　　　　　　　　　　　　　　　$Y$ wherein
X represents

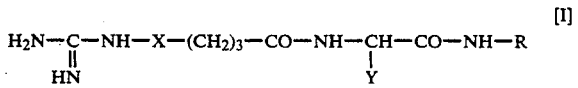

or $-(CH_2)_n-$, Y represents a hydrogen atom or a hydroxyl or hydroxymethyl group,
n is an integer of 3 or 5, and
R represents $-(CH_2)_4-R_1$ (wherein $R_1$ is $-NH_2$ or $-OH$), $-(CH_2)_3-R_2$ (wherein $R_2$ is $-COOH$ or $-CHO$), $-(CH_2)_4-NH-(CH_2)_3-OH$ or $-(CH_2)_4-NH-(CH_2)_2-R_2$ (wherein $R_2$ is as defined above).

9 Claims, No Drawings

IMMUNOPOTENTIATOR AND SPERGUALIN-RELATED COMPOUND THEREFOR

BACKGROUND OF THE INVENTION

Spergualin is a compound which is obtained from a culture broth of *Bacillus laterosporus* and has antitumor and immunosuppressive effects [cf. U.S. Pat. No. 4,518,532 (Japanese Patent Publication No. 23183/1986) and U.S. Pat. No. 4,416,899 and U.S. Pat. No. 4,851,446 (Japanese Patent Laid-Open No. 48957/1982 and No. 129119/1986)] and there have been synthesized a number of compounds related thereto [cf. U.S. Pat. No. 4,556,735 (Japanese Patent Laid-Open No. 185758/1985), EP-A No. 2-0241797 (Japanese Patent Laid-Open No.45247/1988)]. These compounds are expected to be applicable to drugs such as anticancer agents or immunosuppressive agents.

Although several immunopotentiators have been developed so far, none of them is satisfactory, so that there has been urgently required to develop a novel immunopotentiator. Thus the present invention aims at providing a novel immunopotentiator.

SUMMARY OF THE INVENTION

The present invention relates to a novel immunopotentiator which comprises a spergualin-related compound as an active ingredient and a method for potentiating antibody production in a warm-blooded animal.

Further, the present invention provides a novel spergualin-related compound having an immunopotentiating effect.

DETAILED DESCRIPTION OF THE INVENTION

The present inventors have conducted extensive studies and have found out that a spergualin-related compound represented by the following general formula or a pharmacologically acceptable salt thereof:

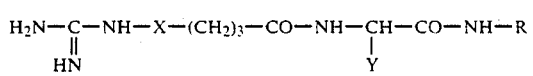

wherein
X represents

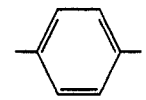

or $-(CH_2)_n-$,
Y represents a hydrogen atom or a hydroxyl or hydroxymethyl group,
n is an integer of 3 or 5, and
R represents $-(CH_2)_4-R_1$ (wherein $R_1$ is $-NH_2$ or $-OH$), $-(CH_2)_3-R_2$ (wherein $R_2$ is $-COOH$ or $-CHO$), $-(CH_2)_4-NH-(CH_2)_3-OH$ or $-(C_6H_4-NH-(CH_2)_2-R_2$ (wherein $R_2$ is as defined above), shows an immunopotentiating effect, thus completing the present invention.

The spergualin-related compound represented by the general formula [I] forms a salt together with an acid. As the acid for the formation of the salt, either an inorganic or an organic acid may be used so long as it has no toxicity. Preferable examples of the inorganic acid include hydrochloric, sulfuric, nitric and phosphoric acids, though the present invention is not restricted thereby. Preferable examples of the organic acid include acetic, propionic, succinic, fumaric, maleic, malic, tartaric, glutaric, citric, benzenesulfonic, toluenesulfonic, methanesulfonic, ethanesulfonic, propanesulfonic, aspartic and glutamic acids, though the present invention is not restricted thereby.

Typical examples of the compound of the present invention represented by the general formula [I] are as follows.

Typical examples of the compound:

$$H_2N-\underset{\underset{HN}{\|}}{C}-NH-X-(CH_2)_3-CO-NH-\underset{\underset{Y}{|}}{CH}-CO-NH-R \quad [I]$$

| Cpd. No. | X | Y | R |
|---|---|---|---|
| 1 | $-(CH_2)_3-$ | OH | $-(CH_2)_4-NH-(CH_2)_3-OH$ |
| 2 | " | | $-(CH_2)_4-NH-(CH_2)_2-COOH$ |
| 3 | " | | $-(CH_2)_4-NH-(CH_2)_2-CHO$ |
| 4 | " | | $-(CH_2)_4-OH$ |
| 5 | " | | $-(CH_2)_3-COOH$ |
| 6 | " | | $-(CH_2)_3-CHO$ |
| 7 | " | | $-(CH_2)_4-NH_2$ |
| 8 | $-(CH_2)_3-$ | H | $-(CH_2)_4-NH-(CH_2)_3-OH$ |
| 9 | " | | $-(CH_2)_4-NH-(CH_2)_2-COOH$ |
| 10 | " | | $-(CH_2)_4-NH-(CH_2)_2-CHO$ |
| 11 | " | | $-(CH_2)_4-OH$ |
| 12 | " | | $-(CH_2)_3-COOH$ |
| 13 | " | | $-(CH_2)_3-CHO$ |
| 14 | " | | $-(CH_2)_4-NH_2$ |
| 15 | $-(CH_2)_3-$ | $-CH_2OH$ | $-(CH_2)_4-NH-(CH_2)_3-OH$ |
| 16 | " | | $-(CH_2)_4-NH-(CH_2)_2-COOH$ |
| 17 | " | | $-(CH_2)_4-NH-(CH_2)_2-CHO$ |
| 18 | " | | $-(CH_2)_4-OH$ |
| 19 | " | | $-(CH_2)_3-COOH$ |
| 20 | " | | $-(CH_2)_3-CHO$ |
| 21 | " | | $-(CH_2)_4-NH_2$ |
| 22 | $-(CH_2)_5-$ | OH | $-(CH_2)_4-NH-(CH_2)_3-OH$ |
| 20 | " | | $-(CH_2)_4-NH-(CH_2)_2-COOH$ |
| 21 | " | | $-(CH_2)_4-NH-(CH_2)_2-CHO$ |
| 22 | " | | $-(CH_2)_4-OH$ |

-continued $$H_2N-\underset{\underset{HN}{\|}}{C}-NH-X-(CH_2)_3-CO-NH-\underset{\underset{Y}{|}}{CH}-CO-NH-R \quad [I]$$

| Cpd. No. | X | Y | R |
|---|---|---|---|
| 23 | " | | —(CH$_2$)$_3$—COOH |
| 24 | " | | —(CH$_2$)$_3$—CHO |
| 25 | " | | —(CH$_2$)$_4$—NH$_2$ |
| 26 | —(CH$_2$)$_5$— | H | —(CH$_2$)$_4$—NH—(CH$_2$)$_3$—OH |
| 27 | " | | —(CH$_2$)$_4$—NH—(CH$_2$)$_2$—COOH |
| 28 | —(CH$_2$)$_5$— | H | —(CH$_2$)$_4$—NH—(CH$_2$)$_2$—CHO |
| 29 | " | | —(CH$_2$)$_4$—OH |
| 30 | " | | —(CH$_2$)$_3$—COOH |
| 31 | " | | —(CH$_2$)$_3$—CHO |
| 32 | " | | —(CH$_2$)$_4$—NH$_2$ |
| 33 | —(CH$_2$)$_5$— | CH$_2$OH | —(CH$_2$)$_4$—NH—(CH$_2$)$_3$—OH |
| 34 | " | | —(CH$_2$)$_4$—NH—(CH$_2$)$_2$—COOH |
| 35 | " | | —(CH$_2$)$_4$—NH—(CH$_2$)$_2$—CHO |
| 37 | " | | —(CH$_2$)$_4$—OH |
| 38 | " | | —(CH$_2$)$_3$—COOH |
| 39 | " | | —(CH$_2$)$_3$—CHO |
| 40 | " | | —(CH$_2$)$_4$—NH$_2$ |
| 41 |  | OH | —(CH$_2$)$_4$—NH—(CH$_2$)$_3$—OH |
| 41 | " | | —(CH$_2$)$_4$—NH—(CH$_2$)$_2$—COOH |
| 42 | " | | —(CH$_2$)$_4$—NH—(CH$_2$)$_2$—CHO |
| 43 | " | | —(CH$_2$)$_4$—OH |
| 44 | " | | —(CH$_2$)$_3$—COOH |
| 45 | " | | —(CH$_2$)$_3$—CHO |
| 46 | " | | —(CH$_2$)$_4$—NH$_2$ |
| 47 | 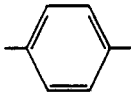 | H | —(CH$_2$)$_4$—NH—(CH$_2$)$_3$—OH |
| 48 | " | | —(CH$_2$)$_4$—NH—(CH$_2$)$_2$—COOH |
| 49 | " | | —(CH$_2$)$_4$—NH—(CH$_2$)$_2$—CHO |
| 50 | " | | —(CH$_2$)$_4$—OH |
| 51 |  | H | —(CH$_2$)$_3$—COOH |
| 52 | " | | —(CH$_2$)$_3$—CHO |
| 53 | " | | —(CH$_2$)$_4$—NH$_2$ |
| 54 | 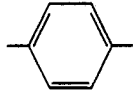 | CH$_2$OH | —(CH$_2$)$_4$—NH—(CH$_2$)$_3$—OH |
| 55 | " | | —(CH$_2$)$_4$—NH—(CH$_2$)$_2$—COOH |
| 56 | " | | —(CH$_2$)$_4$—NH—(CH$_2$)$_2$—CHO |
| 57 | " | | —(CH$_2$)$_4$—OH |
| 58 | " | | —(CH$_2$)$_3$—COOH |
| 59 | " | | —(CH$_2$)$_3$—CHO |
| 60 | " | | —(CH$_2$)$_4$—NH$_2$ |

A compound of the general formula [I] wherein X is (CH$_2$)$_3$— and Y is a hydrogen atom is already known [cf. Umeda et al., J. Antibiotics, 40, 1301-1315 (1987)] while other compounds are novel ones.

The compound of the general formula [I] may be synthesized in the following manner. Namely, a compound represented by the following general formula [II]:

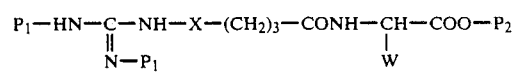

wherein X is as defined above, W represents hydrogen, a protected hydroxy or a protected hydroxymethyl group, P$_1$ represents a hydrogen atom or a protective group, and P$_2$ represents a hydrogen atom or a lower alkyl group, is condensed with a compound represented by the following general formula

NH₂—R wherein R is as defined above, to thereby give the aimed compound.

When P₁ is a hydrogen atom and P₂ is a hydrogen atom, for example, the compound of the general formula [I] may be obtained by the following method (A). When P₁ is a protective group such as Boc and P₂ is a lower alkyl group, the compound of the general formula [I] may be obtained by the following method (B).

Method A:

A compound represented by the following general formula:

$$H_2N-\underset{\underset{NH}{\|}}{C}-NH-X-(CH_2)_3-CO-NH-\underset{W}{CH}-COOH \qquad [II]$$

wherein
X represents

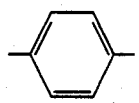

or —(CH₂)ₙ—,

W represents as defined above, and n is an integer of 3 or 5, is condensed with various amines through dehydration and thereafter the protective group in the W group is removed.

A compound represented by the general formula [II] wherein X is —(CH₂)₃— and W is —O—CH₂C₆H₅ is already known and can be synthesized according to a method described in J. Antibiotics, 40, 1316–24 (1987).

Method B:

A compound represented by the following general formula [III]:

$$Boc-HN-\underset{\underset{Boc-N}{\|}}{C}-NH-X-(CH_2)_3CO-NH-\underset{W}{CH}-COOCH_3 \qquad [III]$$

wherein X and W are as defined above, and Boc represents a t-butyloxycarbonyl group which is a protective group of an amino group, is condensed with various amines through elimination of a methanol molecule and then the protective group is removed. A compound of the general formula [III] wherein X is —(CH₂)₃ and W is an OSi(CH₃)₂-t-Bu is already known and may be synthesized by a method described in J. Org. Chem., 52, 1700–1703 (1987).

Examples of the amines to be used in the above methods include 1,4-diaminobutane, 4-amino-1-butanol, 4-aminobutyraldehyde diethyl acetal, ester of 4-aminobutyric acid, 8-amino-1-t-butyloxy-4-t-butyloxycarbonyl-4-azaoctane, N-(3,3-diethoxypropyl)-1,4-butanediamine and ester of 8-amino-4-azaoctanoic acid. Among these amines, 1,4-butanediamine, 4-amino-1-butanol, 4-aminobutyraldehyde diethyl acetal, ester of 4-aminobutyric acid and N-(3,3-diethoxypropyl)-1,4-butanediamine are known compounds which can be readily synthesized by referring to the pertinent literature.

The condensation in the method (A) or (B) may be conducted by a method commonly employed in peptide chemistry. Examples of the method include the carbodiimide method with the use of, for example, dicyclohexylcarbodiimide or 1-ethyl-3-(3'-dimethylaminopropyl-carbodiimide; the mixed anhydride method with the use of, for example, ethyl chlorocarbonate or isobutyl chlorocarbonate; the active ester method with the use of, for example, cyanomethyl ester, vinyl ester, optionally substituted phenyl ester, thiophenyl ester or ester of N-hydroxysuccinimide; the O-acylhydroxylamine derivative method with the use of, for example, acetone oxime or cyclohexanone oxime; the N-acyl compound method with the use of, for example, carbonyldiimidazole; and the carboxylic acid activation method with the use of, for example, 1,3-thiazoline-2-thione.

As the solvent to be used in the condensation, those commonly employed in the formation of a peptide bond may be used. Examples thereof include ethers such as diethyl ether, tetrahydrofuran and dioxane; esters such as ethyl acetate; ketones such as acetone and methyl ethyl ketone; halogenated hydrocarbons such as methylene chloride and chloroform; amides such as dimethylformamide and dimethylacetamide; and nitrides such as acetonitrile. Each of these solvents may be used alone. Alternately, it may be used in the form of a mixture with water, if it is miscible therewith.

Examples of the protective group of an amino group available in the present invention include a benzyloxycarbonyl group, a substituted benzyloxycarbonyl group such as a p-methoxybenzyloxycarbonyl group, a t-butyloxycarbonyl group, a t-amyloxycarbonyl group, a formyl group, a trityl group and an o-nitrophenylsulphenyl group.

On the other hand, examples of the protective group for a carboxyl group include a lower alkyl group, a t-butyl group, a benzyl group and a substituted benzyl group. Examples of the protective group for a hydroxyl group include a t-butyl group, a benzyl group and a t-butyldimethylsilyl group.

The removal of a protective group in the method (A) or (B) may be conducted through, for example, reduction, hydrolysis or acidolysis.

The reaction may be usually conducted in an inert solvent at a temperature of from −60° C. to the boiling point of the solvent, preferably from −50° to 100° C. Examples of the inert solvent include water, hydrophilic organic solvents, lower alcohols such as methanol and ethanol, ketones such as acetone and methyl ethyl ketone, amides such as dimethylformamide and dimethylacetamide, cyclic ethers such as tetrahydrofuran and dioxane, lower aliphatic acids such as acetic acid and trifluoroacetic acid, liquid ammonia and liquid hydrogen fluoride.

A novel spergualin-related compound of the general formula [I] may be isolated from the reaction mixture, in which the protective group has been removed in the above-mentioned manner, by, for example, the following method. When the protective group is removed by catalytic reduction with the use of palladium black, for example, the catalyst is filtered off and the filtrate is concentrated under reduced pressure. Then the residue is purified by a known purification method by using CM-Sephadex® (Na) and Sephadex® LH-20 [cf. Takeuchi et al., J. Antibiotics, 34, 1619 (1981)]. When the protective group is removed by using trifluoroacetic acid, the reaction mixture is concentrated under reduced pressure and the residue is purified in the same manner as the one described above. Thus the aimed product may be isolated.

Thus the novel spergualin-related compound can be obtained in the form of a hydrochloride. This hydrochloride may be converted into a salt of another acid, if desired, in the following manner. Namely, the hydrochloride is dissolved in water and the aqueous solution thus obtained is passed through a strongly basic ion exchange resin. Then fractions containing the aimed compound are combined, neutralized by adding thereto the aimed acid or a solution thereof in water or a hydrophilic organic solvent such as methanol, ethanol, acetone, tetrahydrofuran or dioxane, and then evaporated to dryness under reduced pressure. When the neutralized solution contains an organic solvent, said solvent is distilled off under reduced pressure followed by lyophilizing. Alternately, an aqueous solution of silver hydroxide is added to the hydrochloride of the compound of the general formula [I] so as to neutralize the hydrochloride. Then the insoluble silver chloride is filtered off and a desired acid is added to the filtrate to thereby form a salt which is then lyophilized.

The compound thus obtained sometimes contains a hydrate depending on the treatment conditions.

When the compound of the present invention thus obtained is to be used as a drug, it may be formulated into an oral or a parenteral preparation by compounding with pharmaceutical carrier(s), if required, in a conventional manner. Fillers or carriers are selected from pharmacologically acceptable ones and the type and composition thereof depend on the administration pathway and administration method. For example, a liquid carrier may be selected from among water, alcohols, animal and vegetable oils such as soybean oil and olive oil, mineral oils and synthetic oils. As solid carriers, sugars such as maltose and sucrose, amino acids, cellulose derivatives such as hydroxypropylcellulose and organic acid salts such as magnesium stearate may be employed.

In the case of an injection, it may be dissolved in a solvent preferably selected from among physiological saline, various buffer solutions, solutions of sugars such as glucose, inositol, mannitol and lactose and glycols such as ethylene glycol and polyethylene glycol. Alternately, the spergualin-related compound of the present invention may be lyophilized together with filler(s), for example, sugars such as inositol, mannitol, lactose or sucrose or amino acids such as phenylalanine and the lyophilized preparation thus obtained may be dissolved in an appropriate solvent for intravenous injection, such as sterilized water, physiological saline, a glucose solution, an electrolyte solution or an amino acid solution immediately before the administration. The content of the compound of the present invention in the preparation may vary depending on the dosage form. It may generally range from 0.1 to 100% by weight, preferably 1 to 98% by weight. For example, an injection may preferably contain the active ingredient in an amount of 0.1 to 30% by weight, preferably 1 to 10% by weight. In order to potentiate the immunity of warm-blooded animals including man with the use of the compound of the general formula [I], an effective amount of the compound of the general formula [I] may be administered to the target animal. Thus the antibody production in the animal is potentiated and the immunity of the animal is activated. When the compound of the general formula [I] is to be orally administered, it may be usually formulated into, for example, a tablet, a capsule, a dust, granules, a solution or a dry syrup together with the above-mentioned solid carrier(s) or liquid carrier(s). Capsules, granules or dusts generally contain 5 to 100% by weight, preferably 25 to 98% by weight, of the active ingredient. Although the dose of the compound of the general formula [I] should be determined depending on the age, body weight and conditions of the subject as well as the purpose of the treatment, it may be usually administered at a dose of 1 to 100 mg/kg/day in the case of parenteral administration and at a dose of 5 to 500 mg/kg/day in the case of oral administration.

The following Test Example will be given in order to illustrate the physiological activities of the compound of the present invention.

I. Increasing of antibody production (a) Test method

CDF1-SLC mice (each group comprising five animals) were intravenously immunized with $1 \times 10^8/0.2$ ml of sheep red blood cells (SRBC). From the next day of the immunization, 0.1 ml/10 g/day portions of solutions of the compound of the present invention of various concentrations were intraperitoneally given to these mice daily for three days. To a control group was given physiological saline. On the fourth day after the immunization, the mice were killed and anti-SRBC antibody producing cells (plaque forming cell, PFC) in the spleen cells were counted. Thus the number of PFC per $10^6$ spleen cells was calculated. The effect of the compound of the present invention is expressed in the potentiation ratio (%) of the PFC number of the test group to that of the control group.

$$\text{Potentiation ratio (\%)} = \left( \frac{\text{PFC No. of test group}}{\text{PFC No. of control group}} \right)$$

(b) Increasing of antibody production by the compound of invention

TABLE 1

| Cpd. No. | Increasing of antibody production (control: 100%) | | | *(dose) |
|---|---|---|---|---|
| | 1 mg/kg | 3 mg/kg | 10 mg/kg | |
| 1 | 119 | 116 | 139 | |
| 2 | 114 | 112 | 126 | |
| 4 | 110 | 138 | 135 | |
| 5 | 146 | 148 | 266 | |
| 6 | 123 | 120 | 121 | |
| 7 | 127 | 120 | 126 | |
| 9 | — | 124 | 107 | |
| 12 | — | 133 | 107 | |
| Deoxy-spergualin | 1.56 mg/kg 10 | | 6.25 mg/kg 6 | |
| Control (physological saline) | 100 | 100 | 100 | |

As the above Test Example shows, the compound of the present invention has an excellent immunopotentiating activity and thus expected to be useful as an infection preventive or a remedy for opportunistic infection.

To further illustrate the present invention, and not by way of limiting the scope thereof, the following Examples will be given.

FORMULATION EXAMPLE 1

To 30 parts by weight of the hydrochloride of the compound No. 1 was added an appropriate amount of distilled water for injection to make up to a total amount of 2000 parts by weight. After dissolving the compound, the obtained solution was sterilely filtered through a Millipore filter GS. 2 g of the filtrate was introduced into a vial and lyophilized. Thus a lyophilized preparation for injection containing 30 mg of the hydrochloride of the compound No. 1 per vial was obtained.

FORMULATION EXAMPLE 2

50 parts by weight of the hydrochloride of the compound No. 5, 600 parts by weight of lactose, 330 parts by weight of crystalline cellulose and 20 parts by weight of hydroxypropylcellulose were thoroughly mixed together, compressed with a roller compactor, ground and sieved to collect granules passing through a 16-mesh screen but not a 60-mesh screen.

SYNTHESIS EXAMPLE 1:

Synthesis of 19-guanidino-1,11-dihydroxy-4,9,12-triazadecane-10,13-dione dihydrochloride (compound No. 1)

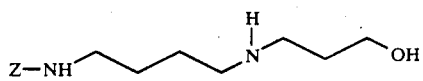

(i) Synthesis of 1-hydroxy-9-benzyloxycarbonyl-4,9-diazanonane:

To 8.8 g (34 mmol) of mono-benzyloxycarbonyl-1,4-butanediamine hydrochloride was added 70 ml of n-butanol. After 8.6 g (84.5 mmol) of triethylamine was added thereto, 5.5 g (58.1 mmol) of 3-chloropropanol was further added thereto. The mixture was allowed to react under reflux overnight. The reaction mixture was then concentrated under reduced pressure and the residue was decanted with ether twice and dissolved in methanol. After filtering off insoluble matters, the filtrate was concentrated under reduced pressure. The crystals thus obtained were decanted with acetone twice and dried. Thus 6.48 g of the aimed compound was obtained in the form of white crystals (yield: 68%).
MP. 116°~120° C.
NMR (CD$_3$OD).
$\delta = 1.2 \sim 2.1$ (m, 7H), 2.7~3.4 (m, 6H), 3.4~3.8 (t, 2H, J=6 Hz), 4.0~8.0 (b, 2H), 5.0 (s, 2H), 7.23 (s, 5H).
TLC (acetone:17% aqueous ammonia = 15:1 v/v).
Rf=0.22

(ii) Synthesis of 1-hydroxy-4-t-butoxycarbonyl-9-benzyloxycarbonyl-4,9-diazanonane:

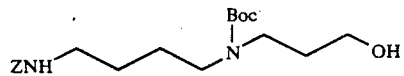

6.48 g (23.1 mmol) of 1-hydroxy-9-benzyloxy-carbonyl-4,9-diazanonane was dissolved in 70 ml of 50% dioxane. After 2.57 g (23.1 mmol) of triethylamine was added thereto, 5.7 g (26.1 mmol) of di-t-butyldicarbonate was further added thereto. The mixture was allowed to react at room temperature for four hours.

To the reaction mixture was added 5 ml of N,N-diethyl-1,3-propanediamine. The mixture was allowed to react at room temperature for 0.5 hour. The reaction mixture was concentrated under reduced pressure and the residue was dissolved in 200 ml of ethyl acetate and washed with distilled water thrice. The organic phase was dried over anhydrous sodium sulfate and the drying agent was filtered off. The filtrate was then concentrated under reduced pressure to thereby give 6.0 g of the aimed compound in the form of an oily product (yield: 63.3%).
NMR (CD$_3$OD).
$\delta = 1.0 \sim 1.9$ (m, 7H), 1.45 (s, 9H), 2.9~3.5 (m, 6H), 3.3~3.7 (t, 2H, J=6 Hz), 4.0~8.0 (b, H), 5.0 (s, 2H), 7.23 (s, 5H).
TLC (chloroform:acetone = 10:1 v/v).
Rf=0.29.

(iii) Synthesis of 1-t-butoxy-4-t-butoxycarbonyl-9-benzyloxycarbonyl-4,9-diazanonane:

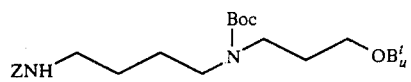

6.0 g (15.77 mmol) or 1-hydroxy-4-t-butoxy-carbonyl-9-benzyloxycarbonyl-4,9-diazanonane was dissolved in a mixture of 30 ml of methylene chloride with 20 ml of dimethylformamide. After adding 0.2 ml of conc. sulfuric acid thereto, the mixture was cooled with dry ice/ethanol. Then isobutylene was added thereto in such an amount as to make up to a total volume of 90 ml and the obtained mixture was allowed to react at room temperature in a pressure bottle overnight. The reaction mixture was cooled, neutralized with triethylamine and concentrated under reduced pressure. The residue was dissolved in 40 ml of 50% dioxane and 1.6 g (15.77 mmol) of triethylamine and 3.44 g (15.77 mmol) of di-t-butyldicarbonate were added thereto. The obtained mixture was allowed to react at room temperature for four hours.

To the reaction mixture was added 3 ml of N,N-diethyl-1,3-propanediamine and the mixture was allowed to react at room temperature for an hour. Next, it was concentrated under reduced pressure and the residue was dissolved in 150 ml of ethyl acetate and successively washed with distilled water, a 5% phosphoric acid solution, a 5% aqueous solution of sodium carbonate and a saturated solution of common salt. The organic phase was dried over anhydrous sodium sulfate and the drying agent was filtered off. Then the filtrate was concentrated under reduced pressure to thereby give 4.5 g of an oily product.

The oily product thus obtained was subjected to column chromatography with the use of Silica gel 60 (Merck Co. & Inc.) and developed with a chloroform/acetone mixture (10:1 v/v). Thus 1.7 g of the aimed compound was obtained in the form of an oily product (yield: 24.7%).
NMR (CD$_3$OD).
$\delta = 1.0 \sim 1.9$ (m, 6H), 1.15 (s, 9H), 1.43 (s, 9H), 2.8~3.5 (m, 8H), 4.0~8.0 (b, H), 5.0 (s, 2H), 7.23 (s, 5H).
TLC (chloroform:acetone = 10:1 v/v).
Rf=0.67.

(iv) Synthesis of 8-amino-1-t-butoxy-4-t-butoxycarbonyl-4-azaoctane:

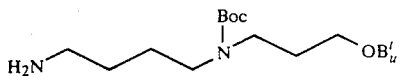

1.6 g (3.66 mmol) of 1-butoxy-4-t-butoxy-carbonyl-9-benzyloxycarbonyl-4,9-diazanonane was dissolved in 25 ml of methanol and 0.25 g of palladium black was added thereto to conduct catalytic reduction at room temperature under atmospheric pressure for three hours.

After the completion of the reaction, the catalyst was filtered off and the filtrate was concentrated under reduced pressure. Thus 1.1 g of the aimed compound was obtained in the form of an oily product (yield: quantitative).

NMR (CD$_3$OD+D$_2$O).

$\delta = 1.0 \sim 2.1$ (m, 6H), 1.15 (s, 9H), 1.43 (s, 9H) 2.4$\sim$2.8 (b, 2H), 2.8$\sim$3.6 (m, 6H).

(v) Synthesis of 19-[2,3-bis(t-butoxycarbonyl)-guanidinol-11-t-butyl-dimethylsilyloxy-4-t-butoxycarbonyl-1-t-butoxy-4,9,12-triazanonadecane-10,13-dione:

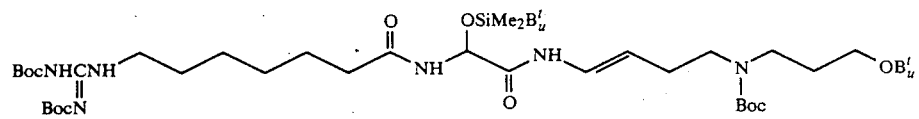

1.1 g (3.63 mmol) of 8-amino-1-t-butoxy-4-t-butoxycarbonyl-4-azaoctane was dissolved in 6 ml of benzene and 2.0 g (3.39 mmol) of methyl 7-[2,3-bis(t-butoxycarbonyl)-guanidino]heptanoyl-α-t-butyldimethylsilyloxy-glycinate was added thereto. The mixture was allowed to react at 39° C. for 40 hours. By concentrating the reaction mixture under reduced pressure, 3.1 g of a pale yellow oily substance was obtained.

The oily product thus obtained was subjected to column chromatography with the use of Silica gel 60 (mfd. by Merck Co. & Inc.) and developed with a mixture of chloroform and ethyl acetate (4:1 v/v). Thus 1.3 g of the aimed compound was obtained in the form of an oily product (yield: 44.7%).

NMR (CD$_3$OD).

$\delta = 0.11$ and 0.21 (2s, 6H), 0.95 (s, 9H), 1.0$\sim$2.0 (m, 14H), 1.2 (s, 9H), 1.5 (s, 18H), 1.54 (s, 9H), 2.0$\sim$2.5 (b, 2H), 2.9$\sim$3.6 (m, 10H), 4.0$\sim$8.0 (b, 4H), 5.66 (s, H), IR (KBr).

$\nu(cm^{-1}) = 3325$, 2930, 2860, 1715, 1685, 1635, 1570, 1520, 1415, 1365, 1330, 1250, 1160, 1135, 1075, 1050, 835, 765.

TLC (chloroform:acetone = 10:1 v/v)

Rf = 0.46.

(vi) Synthesis of 19-guanidino-1,11-dihydroxy-4,9,12-triazadecane-10,13-dione dihydrochloride:

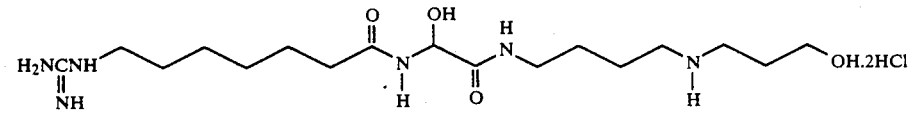

1.2 g (1.39 mmol) of 19-[2,3-bis-(t-butoxycarbonyl)-guanidino]-11-t-butyldimethylsilyloxy-4-t-butoxycarbonyl-1-t-butoxy-4,9,12-triazanonadecane-10,13-dione was dissolved in 1.5 ml of methylene chloride and 8 ml of trifluoroacetic acid was added thereto under ice-cooling. The mixture was allowed to react for five hours. Then the reaction mixture was concentrated under reduced pressure to thereby give 2.1 g of an oily product.

This oily product was then dissolved in 30 ml of distilled water, poured into a column packed with 210 ml of CM-Sephadex ® C-25 (Na$^+$) and subjected to gradient elution between 1100 ml of distilled water and 1100 ml of a 0.2M aqueous solution of sodium chloride. Fractions containing the aimed compound were combined and concentrated to dryness under reduced pressure. To the obtained residue was added 90% ethanol. The insoluble sodium chloride was filtered off and the filtrate was concentrated. The oily product was then dissolved in 4 ml of 90% ethanol. Poured into a column packed with 65 ml of Sephadex ® LH-20 and eluted with 90% ethanol so as to remove the sodium chloride remaining in a small amount. Fractions containing the aimed compound were combined and concentrated under reduced pressure. The oily substance thus obtained was dissolved in 4 ml of distilled water and the insoluble matters were filtered off. After lyophilization, 0.24 g of the aimed compound was obtained (yield: 37.2%).

NMR (D$_2$O, external TMS).

$\delta = 1.5 \sim 2.7$ (m, 14H), 2.5$\sim$3.1 (b, 2H), 3.3$\sim$4.0 (m, 8H), 4.0$\sim$4.4 (t, 2H, J=6 Hz), 5.89 (s, H).

IR (KBr).

$\nu(cm^{-1}) = 3330$, 2950, 2860, 1660, 1650, 1530, 1455, 1060.

TLC (n-propanol:pyridine:water:acetic acid = 6:4:3:2 v/v).

Rf = 0.66.

SYNTHESIS EXAMPLE 2:

Synthesis of 19-guanidino-11-hydroxy-10,13-dioxo-4,9,12-triazanonadecanoic acid hydrochloride (compound No.2):

(i) 4,9-Bisbenzyloxycarbonyl-4,9-diazanonanoic acid:

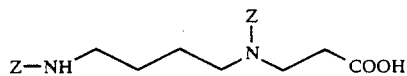

12.7 g (0.10 mol) of N-(2-cyanoethyl)-1,4-butanediamine was dissolved in 100 ml of 6N HCl and heated under reflux for ten hours. The reaction mixture was concentrated to dryness under reduced pressure and the residue was dissolved in 100 ml of distilled water. The pH value of the obtained solution was adjusted to 9 by adding 4N NaOH under ice-cooling. Then 37.5 g (0.22 mol) of carbobenzoxy chloride and 4N NaOH were added dropwise thereto within 30 minutes. During this period, the pH value was maintained at 9 to 10. The reaction mixture was allowed to react for additional 30 minutes, then transferred into a separatory funnel and washed with ether. 6N HCl was added dropwise to the aqueous phase under ice-cooling to adjust the pH value to 2. After extracting with ethyl acetate, the extract was washed with a saturated aqueous solution of common salt and dried over anhydrous sodium sulfate. The ethyl acetate was distilled off to thereby give 35.0 g of the aimed compound in the form of an oily product (yield: 81.7%).

NMR (CD$_3$OD+D$_2$O).

$\delta = 1.0 \sim 1.9$ (4H, br), $2.2 \sim 2.8$ (2H, t, J=7 Hz), $2.8 \sim 3.7$ (6H, m), 4.97 (2H, s), 5.0 (2H, s), 7.22 (10H, s).

(ii) t-Butyl 4,9-bisbenzyloxycarbonyl-4,9-diazanonanoate:

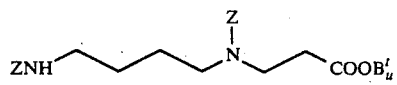

8.9 g (18.67 mmol) of 4,9-bisbenzyloxycarbonyl-4,9-diazanonanoic acid was dissolved in 80 ml of methylene chloride and 0.2 ml of conc. sulfuric acid was added thereto. The obtained mixture was cooled with dry ice/acetone and isobutylene was added thereto in such a amount as to make up to a total volume of 170 ml. Next, the obtained mixture was allowed to react at room temperature in a pressure bottle for 40 hours. The reaction mixture was concentrated under reduced pressure. Thus 9.5 g of an oily product was obtained. The oily product was then subjected to column chromatography with the use of Silica gel 60 (Merck Co. & Inc.) and developed with a mixture of hexane, chloroform and ethyl acetate (6:3:2 v/v). Thus 4.7 g of the aimed compound was obtained in the form of an oily product (yield: 52%).

NMR (CDCl$_3$).

$\delta = 1.2 \sim 1.7$ (4H, m), 1.45 (9H, s), 2.45 (2H, t, J=7 Hz), $2.9 \sim 3.7$ (6H, m), 5.0 (1H, br), 5.04 (2H, s), 5.07 (2H, s), 7.27 (10H, s).

IR$\nu_{max}$ (film)cm$^{-1}$: 3350, 2980, 2940, 1725, 1700, 1530, 1472, 1451, 1420, 1365, 1250, 1150, 700.

Rf 0.29 (chloroform/ethyl acetate, 9:1, v/v).

(iii) t-Butyl 8-amino-4-azaoctanoate:

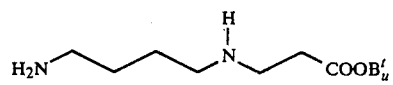

2.49 g (5.14 mmol) of t-butyl 4,9-bisbenzyloxy-carbonyl-4,9-diazanonanoate was dissolved in 20 ml of methanol and 0.3 g of palladium black was added thereto. The obtained mixture was reduced at room temperature under atmospheric pressure in a hydrogen gas stream for three hours. After filtering off the catalyst, the filtrate was concentrated under reduced pressure to thereby give 1.11 g of the aimed compound in the form of an oily product (yield: 100%).

NMR (CDCl$_3$). $\delta: 1.3 \sim 1.8$ (4H, m), 1.46 (9H, s), $2.3 \sim 3.0$ (8H, m). IR$\nu_{max}$(film)cm$^{-1}$: 2990, 2940, 2860, 1728, 1575, 1467, 1365, 1153, 845.

(iv) t-Butyl 11-benzyloxy-19-guanidino-10,13-dioxo-4,9,12-triazanonadecanoate dihydrochloride:

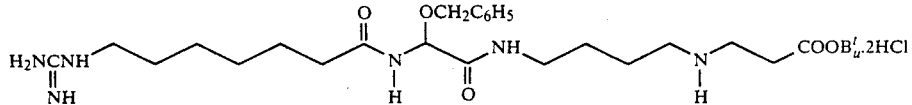

1.5 g (4.28 mmol) of 7-guanidinoheptanoyl-$\alpha$-benzyloxyglycine was dissolved in 10 ml of methanol and 4.28 ml of 1N HCl. After concentrating under reduced pressure, a hydrochloride was obtained. This salt was then dissolved in 24 ml of dimethylformamide and 1.11 g (5.13 mmol) of t-butyl 8-amino-4-azaoctanoate, 0.787 g (5.14 mmol) of 1-hydroxybenzotriazole and 1.15 g (5.56 mmol) of N,N'-dicylcohexylcarbodiimide were added thereto under ice-cooling. The obtained mixture was allowed to react at room temperature overnight and then added to 400 ml of distilled water to thereby dilute the same. The insoluble matters were filtered off and the filtrate was adsorbed on 125 ml of CM-Sephadex® C-25 (Na) and subjected to gradient elution between 500 ml of distilled water and 500 ml of 1N sodium chloride. The target fractions were combined and concentrated to dryness. To the residue was added a mixture of chloroform with methanol (2:1, v/v). After filtering off the insoluble matters, the filtrate was subjected to column chromatography with the use of Silica gel 60 (Merck Co & Inc.). By eluting with a mixture of chloroform and methanol (7:3, v/v) and concentrating under reduced pressure, 1.09 g of the aimed compound was obtained in the form of a vitreous product (yield: 43.5%).

NMR (CD$_3$OD).

$\delta: 1.2 \sim 1.9$ (12H, m), 1.48 (9H, s), 2.28 (2H, t, J=6 Hz), $2.5 \sim 3.3$ (10H, m), 4.61 (2H, s), 5.43 (1H, s), 7.28 (5H, s).

IR$\nu_{max}$(KBr)cm$^{-1}$: 3370, 2940, 1722, 1660, 1526, 1152.

Rf 0.38 (chloroform/methanol, 7:3 v/v).

(v) 19-Guanidino-11-hydroxy-10,13-dioxo-4,9,12-triazanonadecanoic acid hydrochloride:

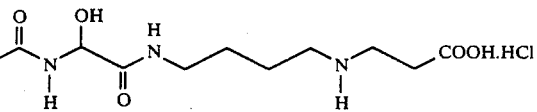

0.95 g (1.53 mmol) of t-butyl 11-benzyloxy-19-guanidino-10,13-dioxo-4,9,12-triazanonadecanoate dihydrochloride was dissolved in 10 ml of trifluoroacetic acid under ice-cooling and then allowed to react at room temperature overnight. The trifluoroacetic acid was distilled off under reduced pressure and the residue was dissolved in 10 ml of distilled water. After washing with 1,2-dichloroethane, the pH value of the product was adjusted to 5.0 with 1N NaOH. Then it was diluted to approximately 2 l with distilled water, adsorbed on 125 ml of CM-Sephadex ® C-25 (Na) and subjected to gradient elution between 1 l of distilled water and 1 l of 0.07M sodium chloride. The target fractions were combined and concentrated to dryness. The insoluble matters were filter off using 90% ethanol and the filtrate was further desalted with 100 ml of Diaion ® HP-20. By eluting with distilled water and lyophilizing, 149.5 mg of the aimed compound was obtained (yield: 22.3%).

NMR (D₂O, external TMS).

$\delta$: 1.6~2.3 (12H, m), 2.70 (2H, t, J=6 Hz), 3.1~3.9 (10H, m), 5.80 (1H, s).

IR$\nu_{max}$(KBr)cm$^{-1}$: 3330, 2930, 1650, 1522, 1386, 1070.

SYNTHESIS EXAMPLE 3:

Synthesis of 19-guanidino-11-hydroxy-4,9,12-triazanonadecane-1,10,13-trione hydrate dihydrochloride (compound No.3):

(i)

19-[2,3-Bis(t-butoxycarbonyl)guanidino]-11-t-butyl-dimethylsilyloxy-1,1-diethoxy-4,9,12-triazanonadecane-10,13-dione:

(ii)

19-Guanidino-11-hydroxy-4,9,12-triazanonadecane-1,10,13-trione hydrate dihydrochloride:

1.32 g (1.70 mmol) of 19-[2,3-bis(t-butoxycarbonyl)-guanidino]-11-t-butyldimethylsilyloxy-1,1-diethoxy-4,9,12-triazanonadecane-10,13-dione was dissolved in 1 ml of methylene chloride and 5 ml of trifluoroacetic acid was added dropwise thereto under ice-cooling. After reacting at room temperature for 2.5 hours, the solvent was distilled off under reduced pressure. The residue was dissolved in 100 ml of distilled water and the pH value of the obtained solution was adjusted to 4.5 with 1N NaOH. The aqueous solution thus obtained was adsorbed on 120 ml of CM-Sephadex ® C-25 (Na) and subjected to gradient elution between 500 ml of distilled water and 500 ml of 0.5M NaCl. Fractions containing the aimed compound were combined, adsorbed on 20 ml of granular Shirasagitan ® KLH-250 and subjected to gradient elution between 500 ml of distilled water and a 50% aqueous solution of acetonitrile. Fractions positive to Sakaguchi's reagent were combined and concentrated under reduced pressure to thereby reduce the volume to one-tenth of the original. Some portion of the concentrate was collected and determined. Thus it was found that the concentrate contained 101 mg of the aimed compound (yield: 12.9%).

NMR (200 MHz, D₂O, TSP).

$\delta$: 1.27~1.42 (4H, m), 1.49~1.82 (8H, m), 1.91~2.04 (2H, m), 2.29 (2H, t, J=7.3 Hz), 3.00~3.40 (8H, m), 5.20 (0.9H, t, J=5.5 Hz), 5.44 (1H, s), 9.69 (0.1H, s).

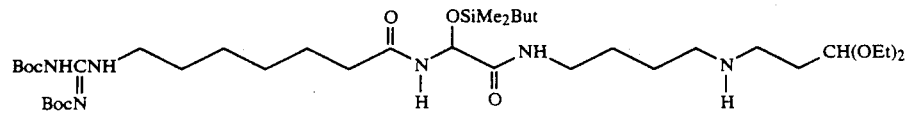

1.57 g (2.67 mmol) of methyl 7-[2,3-bis(t-butoxycarbonyl)guanidinoheptanoyl]-α-t-butyldimethylsilyloxy-glycinate and 0.64 g (2.93 mmol) of N-(3,3-diethoxypropyl)-1,4-butanediamine were dissolved in 5 ml of benzene and stirred at 38° C. for 50 hours. The reaction mixture was then concentrated under reduced pressure and the residue was subjected to column chromatography with the use of Silica gel 60 (mfd. by Merck Co. & Inc.). By eluting with a mixture of chloroform and ethanol (95:5 to 85:15, v/v), 1.58 g of the aimed compound was obtained in the form of an oily product (yield: 76.5%).

NMR (CDCl₃).

$\delta$: 0.11 and 0.21 (6H, 2s), 0.91 (9H, s), 1.18 (6H, t, J=7 Hz), 1.1~2.0 (14H, m), 1.51 (18H, m), 2.20 (2H, t, J=6 Hz), 2.5~2.9 (4H, m), 3.1~3.8 (8H, m), 4.53 (1H, t, J=5.3 Hz), 5.65 (1H, d, J=9 Hz), 6.7~7.0 (2H, br), 8.1~8.4 (1H, br).

IR$\nu_{max}$ (film)cm$^{-1}$: 3330, 2930, 2860, 1719, 1640, 1411, 1363, 1328, 1250, 1152, 1130, 1050, 838, 752.

Rf 0.43 (chloroform/methanol, 4:1, v/v).

SYNTHESIS EXAMPLE 4:

Synthesis of 15-guanidino-1,7-dihydroxy-5,8-diazapentadecane-6,9-dione hydrochloride (compound No.4):

(i)

7-Benzyloxy-15-guanidino-1-hydroxy-5,8-diazapentadecane-6,9-dione hydrochloride:

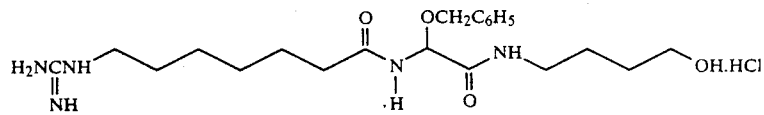

1.0 g (2.85 mmol) of 7-guanidinoheptanoyl-α-benzyloxyglycine was dissolved in 5 ml of methanol and 2.85 ml of 1N HCl and concentrated under reduced pressure to thereby give a hydrochloride. This salt was dissolved in 15 ml of dimethylformamide and 0.305 g (3.42 mmol) of 4-amino-1-butanol, 0.524 g (3.42 mmol) of 1-hydroxybenzotriazole and 0.766 g (3.71 mmol) of N,N'-dicyclohexylcarbodiimide were added thereto under ice-cooling. After reacting at room temperature overnight, the reaction mixture was added to 200 ml of distilled water to thereby dilute the same. The insoluble matters thus formed were filtered off and the filtrate was adsorbed on 100 ml of CM-Sephadex ® C-25 (Na) and subjected to gradient elution between 500 ml of distilled water and 500 ml of 0.8M sodium chloride. Fractions positive to Sakaguchi's reagent were combined and concentrated to dryness. Methanol was added to the residue and the insoluble matters were filtered off. Then the filtrate was subjected to column chromatography with the use of Silica gel 60 (mfd. by Merck Co. & Inc.) and eluted with chloroform/methanol (3:1, v/v). Thus 0.92 g of the aimed compound

SYNTHESIS EXAMPLE 5:

Synthesis of 15-guanidino-7-hydroxy-6,9-dioxo-5,8-diazapentadecanoic acid (compound No.5):

(i) Benzyl 7-benzyloxy-15-guanidino-6,9-dioxo-5,8-diazapentadecanoate hydrochloride:

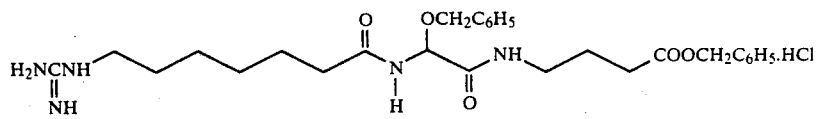

was obtained in the form of an oily product (yield: 77.8%).

NMR (CD$_3$OD).

δ:1.1∼1.9 (12H, m), 2.27 (2H, t, J=6 Hz), 2.9∼3.7 (6H, m), 4.61 (2H, s), 5.48 (1H, s), 7.27 (5H, s).

IR$\nu_{max}$ (film)cm$^{-1}$: 3330, 2930, 1660, 1530, 1065, 1022

Rf 0.50 (chloroform/methanol, 2:1, v/v).

(ii) 15-Guanidino-1,7-dihydroxy-5,8-diazapentadecane-6,9-dione hydrochloride:

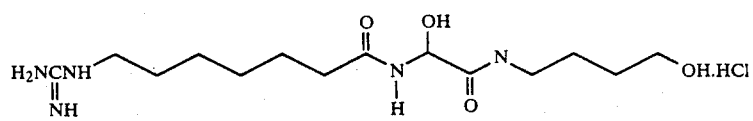

0.65 g (1.42 mmol) of 7-benzyloxy-15-guanidino-1-hydroxy-5,8-diazapentadecane-6,9-dione hydrochloride was dissolved in 20 ml of 1N acetic acid and catalytically reduced in the presence of 0.2 g of palladium black under a hydrogen pressure of 10 kg/cm$^2$ at room temperature for 36 hours. After filtering off the catalyst, the filtrate was adsorbed on 100 ml of CM-Sephadex ® C-25 (Na) and subjected to gradient elution between 500 ml of distilled water and 500 ml of 0.3M sodium chloride. Fractions containing the aimed product were combined and concentrated to dryness under reduced pressure. 90% ethanol was added to the residue and the insoluble sodium chloride was filtered off. The filtrate was then passed through a column packed with 100 ml of Sephadex ® LH-20 and eluted with 90% ethanol. Fractions containing the aimed compound were combined and concentrated to dryness under reduced pressure. The residue was dissolved in a small amount of distilled water and the insoluble matters were filtered off. The obtained aqueous solution was lyophilized to thereby give 0.497 g of the aimed compound (yield: 95.1%).

NMR (D$_2$O, external TMS).

δ:1.7∼2.3 (12H, m), 2.79 (2H, t, J=6 Hz), 3.5∼3.9 (4H, m), 4.08 (2H, t, J=6 Hz), 5.95 (1H, s).

IR$\nu_{max}$(KBr)cm$^{-1}$: 3320, 2930, 2850, 1624, 1535, 1435, 1355, 1260, 1240, 1096, 1078, 1042, 973.

1.0 g (2.85 mmol) of 7-guanidinoheptanoyl-α-benzyloxyglycine, 1.25 g (3.4 mmol) of benzyl 4-aminobutyrate p-toluenesulfonate, 0.48 ml (3.4 mmol) of triethylamine, 0.54 g (3.4 mmol) of 1-hydroxybenzotriazole and 0.77 g (3.7 mmol) of N,N'-dicyclohexylcarbodiimide were condensed together at room temperature overnight. After distilling off the solvent under reduced pressure, the residue was subjected to column chromatography with the use of Silica gel 60 (mfd. by Merck Co. & Inc.). By eluting with chloroform/methanol (10:1–4:1, v/v), 0.90 g of the aimed compound was obtained in the form of a crystalline product (yield: 56.1%). mp 114°∼116° C. (recrystallized from methanol-acetone).

NMR (CD$_3$OD).

δ: 1.1∼1.9 (10H, m), 2.0∼2.5 (4H, m), 2.9∼3.4 (4H, m), 4.59 (2H, s), 5.04 (2H, s), 5.47 (1H, s), 7.27 (10H, s).

IR$\nu_{max}$ (KBr)cm$^{-1}$: 3350, 3280, 3180, 2930, 1735, 1658, 1521, 1172, 690, 562.

Rf 0.43 (chloroform/methanol, 4:1, v/v).

(ii) 15-Guanidino-7-hydroxy-6,9-dioxo-5,8-diazapentadecanoic acid:

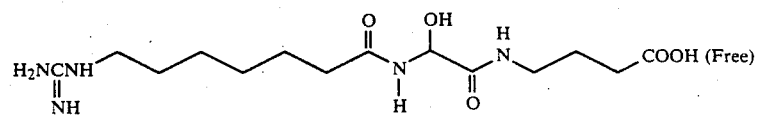

0.79 g (1.41 mmol) of benzyl 7-benzyloxy-15-guanidino-6,9-dioxo-5,8-diazapentadecanoate hydrochloride was dissolved in 10 ml of 1N acetic acid and 10 ml of dimethylformamide and catalytically reduced in the presence of palladium black at room temperature under a hydrogen pressure of 10 kg/cm$^2$ for 34 hours. After filtering off the catalyst, the filtrate was adsorbed on 100 ml of CM-Sephadex ® C-25 (Na) and subjected to gradient elution between 500 ml of distilled water and 500 ml of 0.3M sodium chloride. Fractions containing the aimed compound were combined and concentrated to dryness under reduced pressure. 90% ethanol was added to the residue and the insoluble sodium chloride was filtered off. Next, the filtrate was subjected to gradient elution between 500 ml of distilled water and 500 ml of a 30% aqueous solution of acetone by using a column packed with 100 ml of Diaion ® HP-20. Fractions containing the aimed compound were combined and concentrated under reduced pressure. The residue was dissolved in a small amount of distilled water and the insoluble matters were filtered off. By lyophilizing the product, 0.280 g of the aimed compound was obtained (yield: 57.8%).

NMR (D₂O, external TMS).

δ: 1.7~2.9 (14H, m), 3.5~3.9 (4H, m),

IR$\nu_{max}$(KBr)cm$^{-1}$: 3300, 2920, 1650, 1542, 1390, 1062.

AgNO₃ test: chloride ion (−).

SYNTHESIS EXAMPLE 6:

Synthesis of 15-guanidino-7-hydroxy-5,8-diazapentadacane-1,6,9-trione hydrochloride (compound No.6):

(i)

15-[2,3-Bis(t-butoxycarbonyl)guanidino]-7-t-butyldimethylsilyloxy-1,1-diethoxy-5,8-diazapentadecane-6,9-dione:

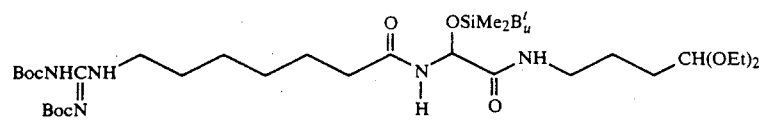

1.80 g (3.06 mmol) of methyl 7-[2,3-bis(t-butoxycarbonyl)-guanidino]heptanoyl-α-t-butyldimethylsilyloxyglycinate and 0.542 g (3.36 mmol) of 4-aminobutyraldehyde diethyl acetal were dissolved in 5.6 ml of benzene and stirred at 38° C. for 51 hours. Then the solvent was distilled off under reduced pressure and the oily substance thus obtained was subjected to column chromatography with the use of Silica gel 60 (mfd by Merck Co. & Inc.). By eluting with chloroform/ethyl acetate (3:2, v/v), 1.39 g of the aimed compound was obtained in the form of an oily product (yield 63.3%).

NMR (CDCl₃).

δ: 0.12 and 0.22 (6H, 2s), 0.92 (9H, s), 1.0~1.8 (12H, m), 1.19 (6H, t, J=7 Hz), 1.52 (18H, s), 2.20 (2H, t, J=7 Hz), 3.1~3.8 (8H, m), 4.45 (1H, br s), 5.66 (1H, d, J=9 Hz), 6.4~6.8 (2H, br), 8.0~8.7 (1H, br), 11.37 (1H, br s).

IR$\nu_{max}$(film)cm$^{-1}$: 3330, 3290, 2980, 2940, 1720, 1640, 1412, 1363, 1332, 1250, 1153, 1130, 1052, 840, 780, 754.

Rf 0.43 (chloroform/ethyl acetate, 1:1, v/v).

(ii)

15-Guanidino-7-hydroxy-5,8-diazapentadecane-1,6,9-trione hydrochloride:

Under ice-cooling, 1.39 g (1.94 mmol) of 15-[2,3-bis(t-butoxycarbonyl)guanidino]-7-t-butyldimethylsilyloxy-1,1-diethoxy-5,8-diazapentadecane-6,9-dione was dissolved in 10 ml of trifluoroacetic acid. After reacting at room temperature for 3.5 hours, the trifluoroacetic acid was distilled off under reduced pressure. The residue was dissolved in 100 ml of distilled water and the pH value of the obtained solution was adjusted to 5.2 with 1N NaOH. The aqueous solution thus obtained was adsorbed on 125 ml of CM-Sephadex ® C-25 (Na) and subjected to gradient elution between 500 ml of distilled water and 500 ml of 0.3M sodium chloride. Fractions containing the aimed compound were combined, adsorbed on 30 ml of granular Shirasagitan ® KLH-250 and subjected to gradient elution between 500 ml of distilled water and 500 ml of 50% aqueous solution of acetonitrile. Fractions positive to Sakaguchi's reagent were combined and concentrated under reduced pressure to thereby reduce the volume to one-tenth of the original. As the result of the determination of some portion of the residue, it was found that the residue contained 336 mg of the aimed compound (yield: 47.4%).

NMR (200 MHz, D₂O, TSP).

δ: 1.26~1.45 (4H, m), 1.50~1.82 (5H, m), 2.00~2.37 (3H, m), 2.31 (2H, t, J=7.2 Hz), 3.16 (2H, t, J=6.8 Hz), 3.20~3.34 (1H, m), 3.53~3.72 (1H, m), 5.47~5.56 (0.7H, m), 5.61~5.72 (0.3H, m), 5.70 (0.3H, s), 5.82 (0.7H, s).

We claim:

1. A use for the preparation of an immunopotentiator of a spergualin-related compound represented by the following general formula [I] or a pharmacologically acceptable salt thereof:

[I]

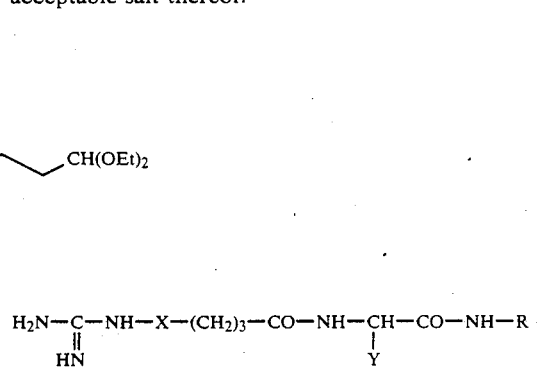

wherein

X represents

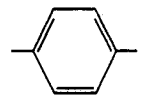

or —(CH₂)$_n$—,

Y represents a hydrogen atom or a hydroxyl or hydroxymethyl group, n is an integer of 3 or 5, and R represents —(CH₂)₄—R₁ (wherein R₁ is —NH₂ or —OH), —(CH₂)₃—R₂ (wherein R₂ is —COOH or —CHO), —(CH₂)₄—NH—(CH₂)₃—OH or (CH₂)₄—NH—(CH₂)₂—R₂ (wherein R₂ is as defined above).

2. A use as claimed in claim 1, wherein X in the general formula [I] is —(CH₂)₃—.

3. A use as claimed in claim 1, wherein X in the general formula [I] is —(CH₂)₃— and (1) Y is —OH and R is —(CH₂)₄—NH—(CH₂)₃—OH, —(CH₂)₄—NH—(CH₂)₂—COOH, —(CH₂)₄—OH, —(CH₂)₃—CHO, —(CH₂)₃—COOH or —(CH₂)₄—NH₂, or (2) Y is a hydrogen atom and R is —(CH₂)₄—NH—(CH₂)₂—COOH or —(CH₂)₃—COOH.

4. A use as claimed in claim 1, wherein the compound of the general formula [I] is:

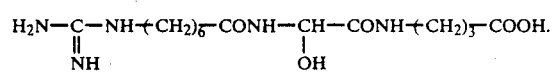

5. A spergualin-related compound represented by the following general formula [I] or a pharmacologically acceptable salt thereof:

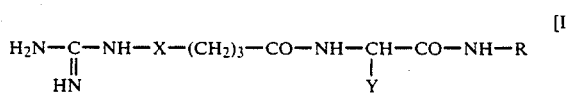

wherein
X represents

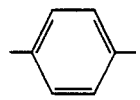

or —(CH$_2$)$_n$—,
Y represents a hydrogen atom or a hydroxyl or hydroxymethyl group,
n is an integer of 3 or 5, provided that the case wherein X is —(CH$_2$)$_3$— and Y is a hydrogen atom is excluded, and
R represents —(CH$_2$)$_4$—R$_1$ (wherein R$_1$ is —NH$_2$ or —OH), —(CH$_2$)$_3$—R$_2$ (wherein R$_2$ is —COOH or —CHO), —(CH$_2$)$_4$—NH—(CH$_2$)$_3$—OH or —(CH$_2$)$_4$—NH—(CH$_2$)$_2$—R$_2$ (wherein R$_2$ is as defined above).

6. A compound as claimed in claim 1, wherein X in the general formula [I] is —(CH$_2$)$_3$— or —(CH$_2$)$_5$— while Y is —OH.

7. A compound as claimed in claim 5, wherein X in the general formula [I] is —(CH$_2$)$_3$—, Y is —OH and R is (1) —(CH$_2$)$_4$—NH—(CH$_2$)$_3$—OH, (2) —(CH$_2$)$_4$—NH—(CH$_2$)$_2$—COOH, (3) —(CH$_2$)$_4$—NH—(CH$_2$)$_2$—CHO, (4) —(CH$_2$)$_4$—OH, (5) —(CH$_2$)$_3$—COOH, (6) —(CH$_2$)$_3$—CHO or (7) —(CH$_2$)$_4$—NH$_2$.

8. A spergualin-related compound represented by the formula:

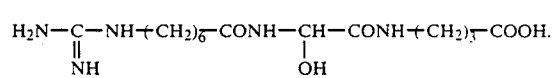

or a pharmacologically acceptable salt thereof.

9. A method for potentiating antibody production in a warm-blooded animal, which comprises administering an effective amount of a spergualin-related compound represented by the following general formula [I] or a pharmacologically acceptable salt thereof:

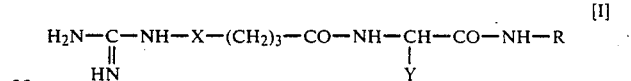

wherein
X represents

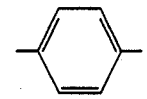

or —(CH$_2$)$_n$—,
y represents a hydrogen atom or a hydroxyl or hydroxymethyl group,
n is an integer of 3 or 5, and
R represents —(CH$_2$)$_4$—R$_1$ group (wherein R$_1$ is —NH$_2$ or —OH), —(CH$_2$)$_3$—R$_2$ (wherein R$_2$ is —COOH or —CHO), —(CH$_2$)$_4$—NH—(CH$_2$)$_3$—OH or —(CH$_2$)$_4$—NH—(CH$_2$)$_2$—R$_2$ (wherein R$_2$ is as defined above), to said animal.

* * * * *